United States Patent
Shan et al.

(10) Patent No.: US 10,529,217 B2
(45) Date of Patent: Jan. 7, 2020

(54) ELECTRIC BED

(71) Applicant: Keeson Technology Corporation Limited, Jiaxing, Zhejiang (CN)

(72) Inventors: Huafeng Shan, Zhejiang (CN); Hui Cao, Zhejiang (CN); Qun Yu, Zhejiang (CN)

(73) Assignee: Keeson Technology Corporation Limited, Jiaxing (CN)

( * ) Notice: Subject to any disclaimer, the term of this patent is extended or adjusted under 35 U.S.C. 154(b) by 0 days.

(21) Appl. No.: 16/052,691

(22) Filed: Aug. 2, 2018

(65) Prior Publication Data

US 2018/0342148 A1    Nov. 29, 2018

Related U.S. Application Data

(63) Continuation of application No. PCT/CN2017/072422, filed on Jan. 24, 2017.

(30) Foreign Application Priority Data

Feb. 2, 2016  (CN) .................... 2016 2 0103449 U

(51) Int. Cl.
*G08B 21/24* (2006.01)
*A47C 21/00* (2006.01)
(Continued)

(52) U.S. Cl.
CPC .............. *G08B 21/24* (2013.01); *A47C 17/86* (2013.01); *A47C 20/041* (2013.01);
(Continued)

(58) Field of Classification Search
None
See application file for complete search history.

(56) References Cited

U.S. PATENT DOCUMENTS 3,934,283 A    1/1976  Raffel
5,107,855 A *  4/1992  Harrington .......... A61B 5/1135
                                              600/534
(Continued)

FOREIGN PATENT DOCUMENTS

CN    104248260 A    12/2014
CN    104706078 A     6/2015
(Continued)

OTHER PUBLICATIONS

International Search Report of PCT Patent Application No. PCT/CN2017/072422 dated Mar. 3, 2017.
(Continued)

*Primary Examiner* — Chico A Foxx

(57) ABSTRACT

An electric bed includes: a bed body, a plurality of bed planks, a wake-up device, a clock and a main control box. The main control box is electrically connected to the wake-up device and the clock, and is applicable for storing a wake-up time. The electric bed further includes a monitoring module. The monitoring module includes a processing module and a sensor, wherein the sensor is electrically connected to the processing module, and is applicable for monitoring whether a user has left the bed; if the sensor monitors that the user has not left the bed, the processing module activates the wake-up device when the wake-up time on the clock is due according to the stored wake-up time; and if the sensor monitors that the user has left the bed, the processing module does not activate the wake-up device when the wake-up time on the clock is due.

9 Claims, 2 Drawing Sheets

(51) Int. Cl.
*G08B 7/06* (2006.01)
*A47C 31/00* (2006.01)
*A61M 21/00* (2006.01)
*A47C 17/86* (2006.01)
*A47C 20/04* (2006.01)
*A61G 7/015* (2006.01)
*A61B 5/00* (2006.01)
*A61B 5/11* (2006.01)

(52) U.S. Cl.
CPC .......... *A47C 21/003* (2013.01); *A47C 21/006* (2013.01); *A47C 31/00* (2013.01); *A61B 5/4809* (2013.01); *A61B 5/6892* (2013.01); *A61G 7/015* (2013.01); *A61M 21/00* (2013.01); *G08B 7/06* (2013.01); *A61B 5/1115* (2013.01)

(56) References Cited

U.S. PATENT DOCUMENTS

| | | | |
|---|---|---|---|
| 6,502,264 B1 | 1/2003 | Clothier et al. | |
| 2005/0227763 A1* | 10/2005 | Lum | A63F 13/06 463/37 |
| 2005/0253912 A1* | 11/2005 | Smith | B41J 2/04553 347/102 |
| 2008/0169931 A1* | 7/2008 | Gentry | A61B 5/1113 340/573.1 |
| 2013/0298332 A1* | 11/2013 | Vanstraelen | A47C 23/067 5/618 |
| 2013/0326814 A1* | 12/2013 | Shan | A47C 20/00 5/613 |
| 2014/0123392 A1* | 5/2014 | Shan | A61G 7/015 5/618 |
| 2014/0259433 A1 | 9/2014 | Nunn et al. | |
| 2015/0128353 A1* | 5/2015 | Kildey | A61M 21/00 5/706 |
| 2015/0359992 A1* | 12/2015 | Sudo | G16H 15/00 600/28 |
| 2016/0007887 A1* | 1/2016 | Shimizu | A61B 5/1115 340/573.4 |
| 2017/0156956 A1* | 6/2017 | Bai | A47C 19/025 |
| 2017/0160703 A1* | 6/2017 | Heo | G04G 13/021 |
| 2018/0000408 A1* | 1/2018 | Heinrich | A61B 5/0452 |
| 2018/0160979 A1* | 6/2018 | Kim | G01L 1/205 |
| 2018/0168485 A1* | 6/2018 | Chen | A61B 5/1113 |

FOREIGN PATENT DOCUMENTS

| | | |
|---|---|---|
| CN | 105231721 A | 1/2016 |
| CN | 105278442 A | 1/2016 |
| JP | 2011092271 A | 5/2011 |

OTHER PUBLICATIONS

The First Examination Report of counterpart Australian Standard Patent Application No. 2017215683 dated Dec. 6, 2018.

* cited by examiner

ELECTRIC BED

CROSS-REFERENCE OF RELATED APPLICATIONS

The present application is a Continuation Application of PCT patent application no. PCT/CN2017/072422 filed on Jan. 24, 2017, which claims the priority of Chinese patent application no. 201620103449.5 filed on Feb. 2, 2016. All the above are hereby incorporated by reference.

FIELD OF TECHNOLOGY

The present application relates to an electric bed, in particular to an electric bed with an intelligent wake-up function.

BACKGROUND TECHNOLOGY

In daily life, people rely on alarm clocks to wake up from their sleep to start a busy day of work life. In order to get rid of the dependence on alarm clocks, people have invented an alarm clock bed with an alarm clock function.

For example, patent document CN104248260 disclosed a foldable alarm clock bed, which includes an integral formed from a timer, a piston control rod and a support rod. When a set time on the timer is due, the piston control rod folds a foldable bed plank and props up the support rod. People sit up with the folded bed plank, thus realizing the function of an alarm clock.

Further, patent document CN104706078 disclosed an alarm clock bed, which includes a bed body and a vibrator. After a user sets a wake-up time using an electronic operation screen on the bed body, the vibrator starts to vibrate at the set time to wake up the user, and the user needs to unlock the electronic operation screen to prevent the vibrator from continuing vibrating.

However, in the above two prior technical solutions, the existing alarm clock beds only start to operate according to the set alarm time and disregard whether there is anyone on the bed.

When the user travels or goes out for a business trip, the bed will always be folded or in a vibration state, which brings unnecessary troubles to the user. Also, the user needs to manually set the alarm clock bed in order to restore it to an initial state, so it is very inconvenient to use.

In addition, setting alarm time on the timer or the electronic operation screen on the bed body is quite inflexible. In particular, when a user needs to travel urgently or go out on an emergency, the alarm time that has been set cannot be changed in time. This leads the alarm clock bed to still perform the folding or vibration alarm function even the user is not at home, which brings unnecessary troubles to the user.

SUMMARY

It is to be noted that the purpose of the present application is to overcome one or more of the disadvantages that have been found in the prior art, and to provide an electric bed capable of detecting whether a user has left the bed, thereby automatically determining whether to activate an alarm clock. The electric bed reduces the trouble caused by performing an alarm function even a user has left the bed. In addition, the electric bed can customize an alarm time and an alarm mode, which improves a user's personalized experience.

For this purpose, an electric bed with an intelligent wake-up function is proposed according to the present application, which is realized by the following technical solutions:

An electric bed, including a bed body, a plurality of bed planks, a wake-up device, a clock and a main control box, the main control box being electrically connected to the wake-up device and the clock and adapted to store a wake-up time, wherein the electric bed further includes a monitoring module including a processing module and a sensor, wherein: the sensor is electrically connected to the processing module, and is adapted to monitor whether a user has left the bed; if the sensor monitors the user has not left the bed, the processing module activates the wake-up device when the wake-up time on the clock is due according to the stored wake-up time; and if the sensor monitors that the user has left the bed, the processing module does not activate the wake-up device when the wake-up time on the clock is due.

By the above setting, the electric bed can grasp the information of whether the user has left the bed, and according to the information, decide whether to perform the wake-up function, which solves the trouble in the prior art that an alarm clock bed executes the alarm program even if the user has left the bed.

Further, the sensor is a thin film pressure sensor provided on the plurality of bed planks. The thin film pressure sensor can reliably detect whether the user is lying on the bed to ensure the reliability of the main control box to independently determine whether to perform the wake-up function.

Further, the wake-up device is a driver for driving one of the plurality of bed planks to rotate, one end of the driver is hinged to the bed body, and another end of the driver is hinged to a bed plank to be driven, and when the driver is activated by the main control box, the driver drives the bed plank hinged thereto to rotate. By this setting, the electric bed can wake up the user by rotating the bed planks.

Further, the wake-up device is a vibration massager, and the vibration massager is provided to at least one of the plurality of bed planks. By this setting, the electric bed can wake up the user by means of vibration massage.

Further, the wake-up device is a sounding device provided in the bed body. By this setting, the electric bed can wake up the user by means of sounding.

Further, the wake-up device is a light-emitting device provided in the bed body. By this setting, the electric bed can wake up the user by means of lighting.

Further, the wake-up device is at least two or more selected from the group consisting of a driver for driving one of the plurality of bed planks to rotate, a vibration massager provided to at least one of the plurality of bed planks, a sounding device and a light-emitting device, and wherein the main control box is further adapted to store a wake-up mode and select a required wake-up device according to a stored wake-up mode. By this setting, the electric bed integrates multiple wake-up modes of rotating bed plank to wake up the user and vibration massager to wake up the user, can also wake up the user by sounding and lighting, and can adapt to the needs of different users, especially hearing-impaired patients. In addition, the user's personalized experience can be further improved by customizing the rotating angle of the bed planks and the vibration intensity of the vibrating massager.

Further, the electric bed further includes a wireless communication module, the wireless communication module is electrically connected to the main control box, and the wireless communication module is wirelessly connected to an intelligent terminal, the intelligent terminal sets and transmits a wake-up time and a wake-up mode to the wireless communication module by a user, and the wireless communication module receives and transmits the wake-up time and the wake-up mode to the main control box. By setting in this way, the degree of freedom for the user setting the wake-up parameters is greatly improved, and the limitation that a user must be limited to setting the alarm time around the bed body in the existing alarm clock bed is eliminated, so that the user can set it anytime and anywhere.

Further, the monitoring module further includes a physical condition monitoring module, the physical condition monitoring module is configured to monitor physical parameters of the user and transmit the physical parameters to the processing module, wherein the processing module further determines, according to the received physical parameters, whether to wake up the user at the wake-up time in order to provide a more personalized service for the user.

Further, the monitoring module is wiredly connected with the wireless communication module and communicating with each other in both directions, and the wireless communication module is wiredly connected with the main control box and adopts serial communication.

With the above arrangements, the electric bed of the present application provides a plurality of wake-up modes that can be selected alone or in combination, and can independently determine whether a user has left the bed, avoiding the situation where people have already woke up and the wake-up mode is still activated, thereby achieving intelligence and the purpose of saving electricity. In addition, physical parameters of the user can be monitored using the physical condition monitoring module of the present application. In combination with the above parameters, various wake-up modes can be set by setting parameters, which improves user experience. In addition, by setting the wake-up time and the wake-up mode through the intelligent terminal, the wake-up time and the wake-up mode can be adjusted anytime and anywhere, which increases the user's operation freedom.

BRIEF DESCRIPTION OF THE DRAWINGS

It should be understood that in the present application, all features, modifications, and/or embodiments may be combined in various combinations, except in the cases of obvious contradictions and incompatibilities.

By reading the following non-limiting illustrative embodiments, and in conjunction with the drawings, other features and advantages of the present application will become apparent. In the figures.

DETAILED DESCRIPTION

Figure 1:
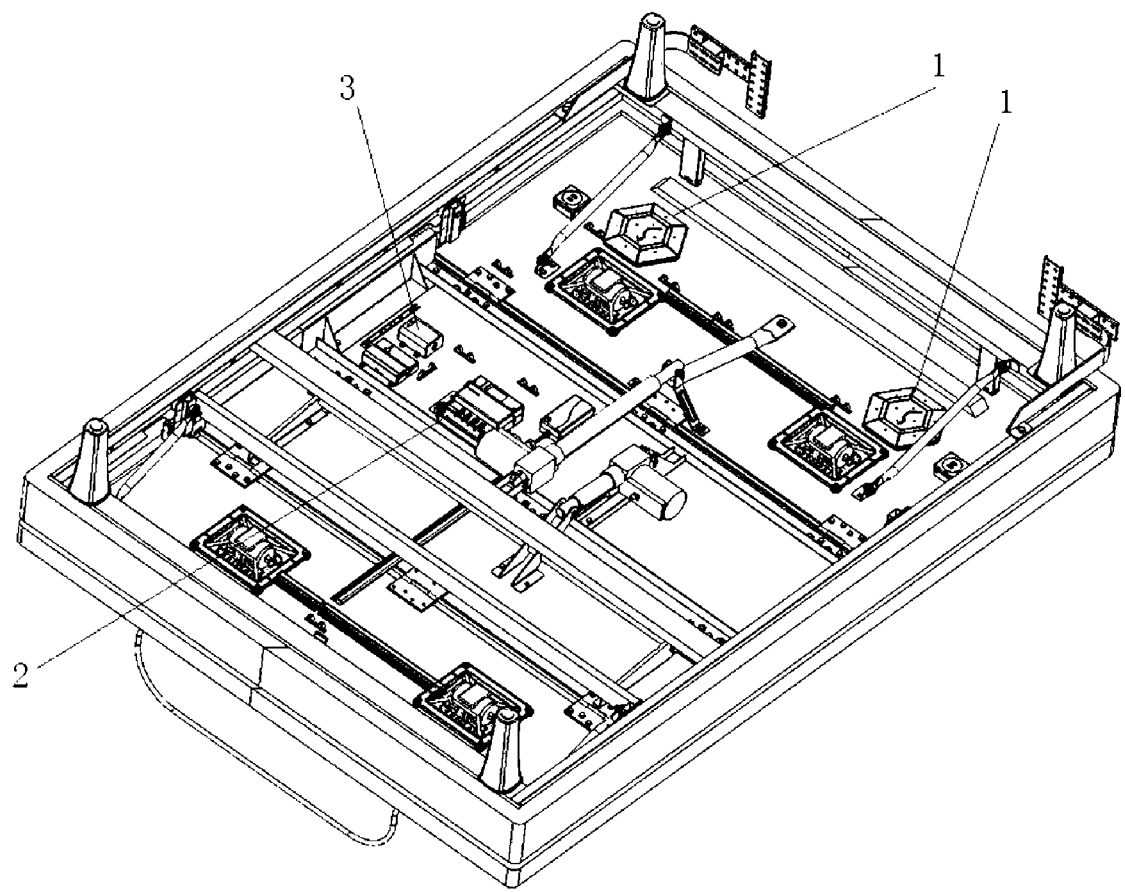
FIG. 1 is a schematic structural view showing an electric bed with an intelligent wake-up function according to the present application.

It should be understood that the abovementioned drawings are not drawn to actual scale, but are merely schematic representations of various preferred features for illustrating the basic principles of the present application. The design features disclosed in the present application, such as size, orientation, position, and shape, are determined based on specific applications and use environments.

The present application will be described in detail below with reference to the embodiments and the accompanying drawings. In these figures, the same reference numerals are used to refer to the same or equivalent elements of the present application in the drawings.

With reference to FIG. 1, an electric bed according to an embodiment of the present application is shown. The electric bed includes a bed body and a plurality of bed planks. These bed planks include at least a head bed plank, a waist bed plank, a leg bed plank and a foot bed plank. These bed planks are hinged to each other by hinges. Below the head bed plank and the foot bed plank are respectively provided with a driver for driving the head bed plank and the head bed plank to rotate and a linkage mechanism for working with the driver. When the head bed plank and the foot bed plank are rotated, their respective linkage mechanisms play a guiding role in their predetermined strokes and play a supporting role after the head bed plank and the foot bed plank are moved into position, thereby ensuring that the rotation of the bed planks is reliable and that a user lying on the bed plank after rotating in place is safe.

In the present embodiment, a vibration massager is also provided in the head bed plank and the foot bed plank, and the vibration massager can be any currently existing vibrator having a massage function. In a modification of the present embodiment, a vibration massager can also be provided in the waist bed plank and the leg bed plank.

Optionally, a light-emitting device, such as a common lamp, a display screen, and the like, is also installed in the bed body.

Optionally, a sounding device, such as a common alarm clock, a speaker, and the like, is also installed in the bed body.

The driver, the vibration massager, the light-emitting device, and the sounding device described above as a wake-up device of the electric bed can be used alone or in combination according to a user's preference.

The electric bed also includes a main control box 2 electrically connected to the driver for driving the head bed plank and the foot bed plank as well as the vibration massager to control operation of the driver and the vibration massager according to a control program. Similarly, if a light-emitting device and/or a sounding device are installed in the bed body, the main control box is also electrically connected to the light-emitting device and/or the sounding device to control operation of the light-emitting device and/or the sounding device according to the control program. In particular, the main control box is provided in the bed body below the bed planks to achieve an aesthetic effect.

In addition, a thin film pressure sensor is also provided on the bed planks of the electric bed. Preferably, a thin film pressure sensor is provided on each of the bed planks. The thin film pressure sensor is electrically connected to the main control box, and monitored pressure value is input into the main control box in real time, so that the main control box determines whether a user has left the bed. The main control box is configured such that when the thin film pressure sensor detects that the user has not left the bed, it allows the main control box to activate the wake-up function; and when the thin film pressure sensor detects that the user has left the bed, it does not allow the main control box to activate the wake-up function.

The electric bed further includes a wireless communication module 3 electrically connected with the main control box. The wireless communication module is adapted to be connected with an external intelligent terminal by means of wireless connection, such as Wi-Fi, Bluetooth, infrared, ZigBee, 2G, 3G, 4G or the Internet. The user sets and transmits wake-up parameters to the wireless communication module of the electric bed through the intelligent terminal, and then the wireless communication module transmits the wake-up parameters sent by the intelligent terminal to the main control box, so that the main control box controls the driver and the vibration massager according to the requirements of the wake-up parameters.

Typically, wake-up time and wake-up mode can be set up in the intelligent terminal. The difference from the existing alarm clock beds is that the wake-up time set in the present embodiment can be a period of time between the start time and the end time instead of limited to a certain moment. The electric bed of the present application not only wakes up a user at a specific wake-up time, but selects the best moment to wake up the user in the wake-up time period from the start time to the end time, so that the user will not feel annoyed and anxious after getting up. To this end, the present embodiment also includes a monitoring module 1, which will be described in detail below.

The monitoring module includes: the abovementioned sensor, a processing module, and a physical condition monitoring module. According to special physical changes, specifically, during deep sleep, muscles of a human body relax and limbs will not give large movements, or even move; during light sleep, a human body will give certain slight movements; and large body movements often occur in a transition of light sleep and wakefulness processes. Through the body movements, it can be determined whether a user is about to wake up. The physical condition monitoring module is electrically connected to the main control box, and sends physical parameters of the user to the main control box in real time during the set wake-up time period. The main control box starts the preset wake-up mode when the user is about to wake up according to a predetermined program to help the user to wake up.

Wherein, the wake-up mode mainly includes rotating the head bed plank and/or the foot bed plank to a certain angle or raising a certain height to assist the user to get up, or performing a mild or moderate massage in the morning using the vibration massager, or giving a gradual sound or light to wake up the user, helping the user to quickly enter an energetic state and improve efficiency of the whole day.

In the present embodiment, the monitoring module is wiredly connected to the wireless communication module and communicates with each other in both directions.

The wireless communication module is a Wi-Fi module, and, depending on cases, may also be a Bluetooth module, an infrared module, a ZigBee module, a 2G module, a 3G module, a 4G module, or an Internet networking module, etc., in order to wirelessly connect with the intelligent terminal. The wireless communication module is adapted to receive a control signal sent by the intelligent terminal and forward it to the main control box to determine the operation to be performed by the main control box.

Optionally, the wireless communication module feeds back status information of the main control box to the intelligent terminal, and the wireless communication module is wiredly connected with the main control box and adopts serial communication.

The intelligent terminal includes a mobile phone, a tablet computer, a notebook computer, etc. The intelligent terminal is installed with an application (App) and/or software for controlling the electric bed. Using the installed application (App) and/or software, the intelligent terminal controls a wireless module inside the intelligent terminal to transmit a control signal carrying a command Both the type of the wireless module of the intelligent terminal and the type of the wireless communication module of the electric bed are a Wi-Fi module, and, depending on cases, may also be a Bluetooth module, an infrared module, a ZigBee module, or the like. Such application (App) and/or software include a human-computer interaction interface, on the one hand including a control command option interface for user's selection, and on the other hand a display interface that provides the user a first measured value information. The user can select/set functions to be controlled by clicking, double clicking, sliding, touching, and inputting values.

The user can set the wake-up time through the intelligent terminal. The intelligent terminal has a built-in clock. When the wake-up time is approaching/due, a control signal is sent to the electric bed to activate the set wake-up mode, such as starting the drive to gradually lift the bed planks, or starting the vibration massage, or lighting or sounding, or simultaneously starting two or more of them.

Of course, a clock can also be provided in the main control box or wireless communication module.

If the main control box has a built-in clock, the user stores the wake-up time and the wake-up mode in the intelligent terminal through the intelligent terminal, and transmits the wake-up time and the wake-up mode to the wireless communication module by wireless transmission. When the wake-up time is due, the main control box sends a control signal to control operation of a motor and massage by the bed body, or to wake up the user by lighting or sounding.

If the wireless communication module has a built-in clock, the user stores the wake-up time and the wake-up mode in the intelligent terminal through the intelligent terminal, and transmits the wake-up time and the wake-up mode to the wireless communication module by wireless transmission. When the alarm time is due, a control signal is sent to the main control box, and the main control box controls operation of a motor and massage by the bed body, or wakes up the user by lighting or sounding.

Figure 2:
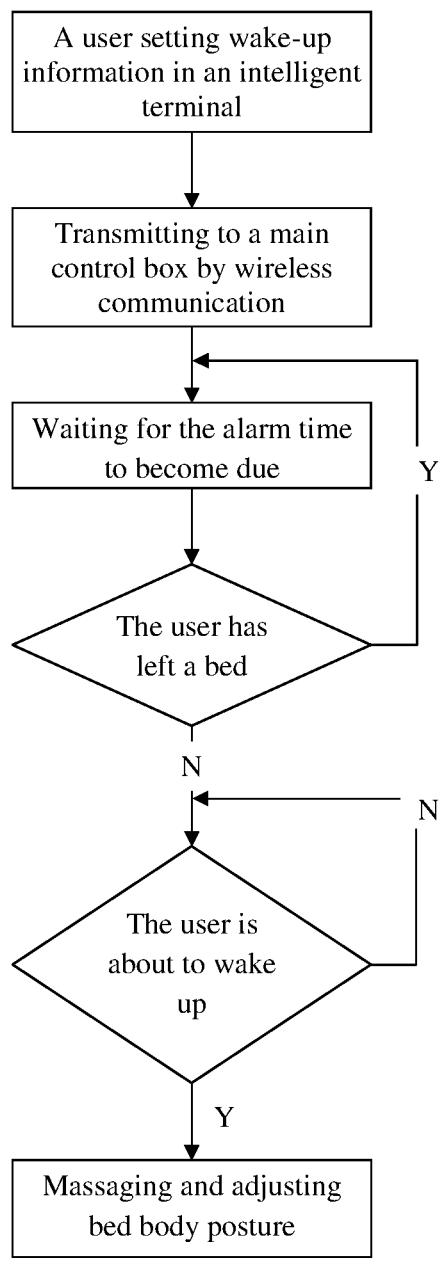
FIG. 2 is a flow chart showing the operation of the intelligent wake-up function of FIG. 1.

As shown in FIG. 2, a flow chart of working steps of the electric bed of the present application when performing the intelligent wake-up function is shown.

Step 1: A user stores a wake-up time and a wake-up mode into the intelligent terminal;

Step 2: The intelligent terminal transmits the wake-up time and the wake-up mode to the wireless communication module by means of wireless communication;

Step 3: Waiting for the alarm time to become due and determining whether the user has left the bed; if so, not processing;

Step 4: When the user is in bed, determining whether the user is about to wake up according to sleep information fed back by the monitoring module; if so, waking up the user according to the wake-up mode set by the user, otherwise continuing to wait.

Wherein, if the user sets massage as the wake-up mode, the main control box wakes up the user by massage.

If the user sets adjustment of bed body posture as the wake-up mode, the main control box wakes up the user by adjusting the bed body posture.

If the user sets massage and adjustment of bed body posture as the wake-up mode, the main control box wakes up the user by massage and adjusting the bed body posture.

In addition, the user can also set lighting or sounding as the mode for waking up the user.

The above embodiments are merely examples and do not limit the scope of the present application. Based on this, those skilled in the art can envision other embodiments that can achieve the same function within the scope of the claims of the present application.

Various embodiments and various modifications and improvements will be apparent to those skilled in the art. In particular, it should be understood that the above-described features, modifications, and/or embodiments of the present application may be combined with each other, except in the case of obvious contradictions or incompatibilities. All of these embodiments, as well as variations and modifications, are within the scope of the present application.

What is claimed is:

1. An electric bed, comprising a bed body, a plurality of bed planks, a wake-up device, a clock and a main control box, the main control box being electrically connected to the wake-up device and the clock and adapted to store a wake-up time, wherein the electric bed further comprises a monitoring module comprising a processing module and a sensor, wherein:
   the sensor is electrically connected to the processing module, and is adapted to monitor whether a user has left the bed; if the sensor monitors the user has not left the bed, the processing module activates the wake-up device when the wake-up time on the clock is due according to the stored wake-up time; and if the sensor monitors that the user has left the bed, the processing module does not activate the wake-up device when the wake-up time on the clock is due;
   wherein the monitoring module monitors large body movements occurring in a transition of light sleep and wakefulness processes and sends physical parameters of the user to the main control box in real time during a set wake-up time period; and
   the main control box starts a preset wake-up mode when the user is about to wake up according to a predetermined program;
   wherein the plurality of bed planks comprises at least a head bed plank, a waist bed plank, a leg bed plank and a foot bed plank hinged to each other by hinges;
   the wake-up device comprises drivers respectively provided below the head bed plank and the foot bed plank for driving the head bed plank and the foot bed plank to rotate and linkage mechanisms for respectively working with the drivers;
   when the head bed plank and the foot bed plank are rotated by respective drivers, respective linkage mechanisms of the head bed plank and the foot bed plank guide the head bed plank and the foot bed plank in predetermined strokes, and support the head bed plank and the foot bed plank after the head bed plank and the foot bed plank are moved into position.

2. The electric bed according to claim 1, wherein the sensor is a thin film pressure sensor provided on the plurality of bed planks.

3. The electric bed according to claim 2, wherein the wake-up device is a driver for driving one of the plurality of bed planks to rotate, one end of the driver is hinged to the bed body, and another end of the driver is hinged to a bed plank to be driven, and when the driver is activated by the main control box, the driver drives the bed plank hinged thereto to rotate.

4. The electric bed according to claim 2, wherein the wake-up device is a vibration massager, and the vibration massager is provided to at least one of the plurality of bed planks.

5. The electric bed according to claim 2, wherein the wake-up device is a sounding device provided in the bed body.

6. The electric bed according to claim 2, wherein the wake-up device is a light-emitting device provided in the bed body.

7. The electric bed according to claim 2, wherein the wake-up device further comprises at least one or more selected from the group consisting of a vibration massager provided to at least one of the plurality of bed planks, a sounding device and a light-emitting device, and wherein the main control box is further adapted to store a wake-up mode and select a required wake-up device according to a stored wake-up mode.

8. The electric bed according to claim 1, wherein the electric bed further comprises a wireless communication module, the wireless communication module is electrically connected to the main control box, and the wireless communication module is wirelessly connected to an intelligent terminal, the intelligent terminal sets and transmits a wake-up time and a wake-up mode to the wireless communication module by a user, and the wireless communication module receives and transmits the wake-up time and the wake-up mode to the main control box.

9. The electric bed according to claim 8, wherein the monitoring module is wiredly connected with the wireless communication module and communicating with each other in both directions, and the wireless communication module is wiredly connected with the main control box and adopts serial communication.

* * * * *